United States Patent
Katsumura et al.

(10) Patent No.: US 7,232,914 B2
(45) Date of Patent: Jun. 19, 2007

(54) SPHINGOMYELIN ANALOGUES AND A PROCESS FOR PREPARATION THEREOF

(75) Inventors: Shigeo Katsumura, Hyogo-ken (JP); Toshikazu Hakogi, Hyogo-ken (JP); Toshihiko Shigenari, Osaka-fu (JP)

(73) Assignee: Daiso Co., Ltd, Osaka-Fu (JP)

( * ) Notice: Subject to any disclaimer, the term of this patent is extended or adjusted under 35 U.S.C. 154(b) by 206 days.

(21) Appl. No.: 11/074,837

(22) Filed: Mar. 9, 2005

(65) Prior Publication Data

US 2006/0008518 A1    Jan. 12, 2006

(30) Foreign Application Priority Data

Jul. 6, 2004  (JP)  ............... 2004-199484

(51) Int. Cl.
*C07D 229/02*  (2006.01)
*C07D 203/04*  (2006.01)
(52) U.S. Cl. ................. 548/960; 548/954
(58) Field of Classification Search ......... 548/954, 548/960
See application file for complete search history.

(56) References Cited

OTHER PUBLICATIONS

Abstract of "84th Spring Meeting of the Chemical Society of Japan", published Mar. 11, 2004.
Abstract of "33rd Symposium of Heterocyclic Chemistry", published Sep. 19, 2003.
U.S. Appl. No. 10/934,571.

*Primary Examiner*—J. Parsa
(74) *Attorney, Agent, or Firm*—Wenderoth, Lind & Ponack, L.L.P.

(57) ABSTRACT

A sphingomyelin analog represented by the following formula (1)

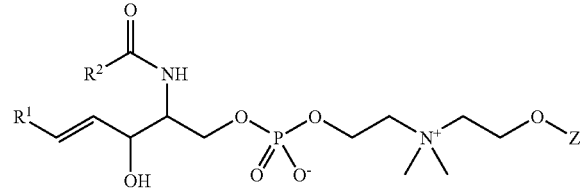

wherein $R^1$ is $C_{1-20}$ alkyl group, $R^2$ is $C_{1-20}$ alkyl group, aryl group or $C_{1-6}$ alkyl group substituted by aryl group, and Z is photoaffinity-labeled group,
or its optically active compound.

9 Claims, No Drawings

SPHINGOMYELIN ANALOGUES AND A PROCESS FOR PREPARATION THEREOF

TECHNICAL FIELD

The present invention relates to a photoaffinity-labeled sphingomyelin analog, its intermediate and its process.

BACKGROUND ART

Metabolites of sphingomyelin, sphingolipids such as ceramide, sphingosine or sphingosine 1-phosphate, participate in intracellular signal translation, such as apoptosis, cell proliferation, PKC inhibition, etc., and therefore the metabolites have drawn the great attention. From the fact, the enzyme, sphingomyelinase which converts sphingomyelin to ceramide is considered to be a very important enzyme.

However, the mechanism of action and the higher-order structure of this enzyme are not elucidated and therefore, such a substance as useful for a resolution of the mechanism, etc., has been desired.

The present inventors designed photoaffinity-labeled sphingomyelin analogs and prepared them in order to investigate the mechanism of action of sphingomyelinase. The result of the study was reported on the 33rd Symposium of Heterocyclic chemistry (See the abstract of the 33rd Symposium of Heterocyclic chemistry, page 42-43, issued on Sep. 19, 2003). However, the compounds disclosed therein are sphingomyelins having a photoaffinity-labeled group at their main chain or their N-terminus of the acyl group, and the photoaffinity-labeled group is hydrophobic. The group is quite separated from the phosphate, and therefore it is not considered that such compounds are most suitable for resolution of the mechanism. Therefore, the development of the compound which is useful for more effective resolution of the mechanism of sphingomyelinase has been desired.

DISCLOSURE OF THE INVENTION

The present inventors have studied hard and as a result, found that a photoaffinity-labeled sphingomyelin analog represented by the following formula (1) can achieve the object mentioned above and the compounds can be effectively synthesized by the method of the present invention.

The present invention relates to a sphingomyelin analog represented by the following formula:

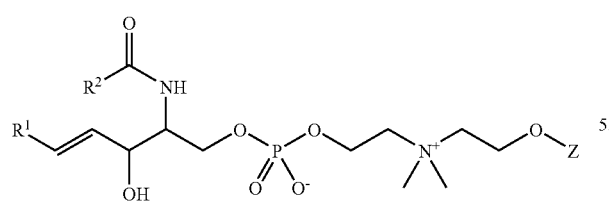

wherein $R^1$ is $C_{1-20}$ alkyl group, $R^2$ is $C_{1-20}$ alkyl group, aryl group or $C_{1-6}$ alkyl group substituted by aryl group, and Z is photoaffinity-labeled group, or its optically active compound.

The present invention also relates to a process for preparing the sphingomyelin analog represented by the following formula:

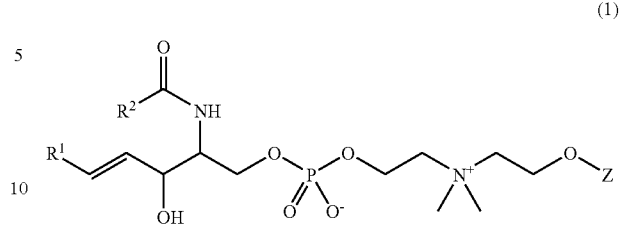

wherein $R^1$, $R^2$ and Z are the same as defined above, or its optically active compound which comprises deprotecting the protecting amino group of a compound represented by the following formula:

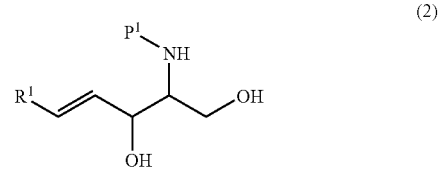

wherein $P^1$ is amino protecting group, and $R^1$ is the same as defined above, amidating the amino group to obtain a compound of the following formula:

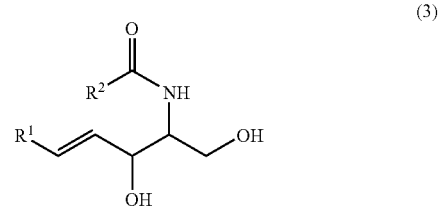

wherein $R^1$ and $R^2$ are the same as defined above, protecting the primary alcohol to obtain a compound of the following formula:

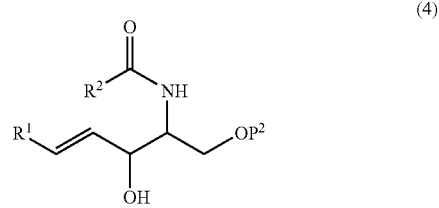

wherein $P^2$ is hydroxy protecting group, and $R^1$ and $R^2$ are the same as defined above, protecting the secondary alcohol, deprotecting the protecting group of the primary alcohol to obtain a compound of the following formula:

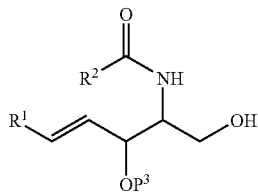

(5)

wherein $P^3$ is hydroxy protecting group, $R^1$ and $R^2$ are the same as defined above, reacting the compound (5) with a compound of the following formula:

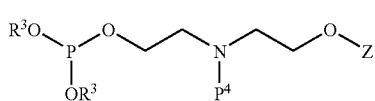

(6)

wherein $R^3$ is $C_{1-6}$ alkyl group, $P^4$ is amino protecting group, and Z is the same as defined above, deprotecting the amino protecting group to obtain a compound of the following formula:

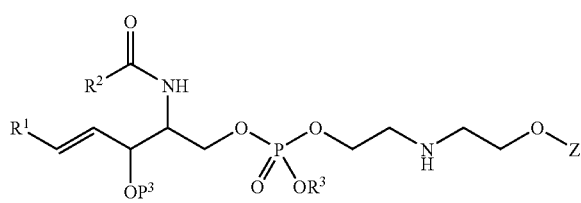

(7)

wherein $R^1$, $R^2$, $R^3$, $P^3$ and Z are the same as defined above, hydrolyzing the phosphate moiety of the compound (7), methylating the amino group of the compound (7) and then deprotecting the protecting group of the secondary alcohol of the compound (7) to obtain the compound (1).

The present invention also relates to a process for preparing the compound of the following formula:

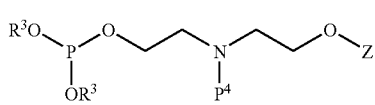

(6)

wherein $R^3$, $P^4$ and Z are the same as defined above, which comprises reacting a compound of the following formula:

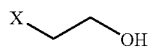

(8)

wherein X is halogen atom, with a compound having photoaffinity-labeled group, to obtain a compound of the following formula:

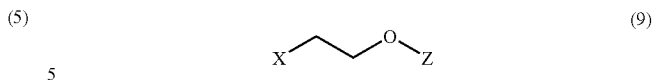

(9)

wherein X and Z are the same as defined above, reacting the compound (9) with 2-aminoethanol, protecting the amino group to obtain a compound of the following formula:

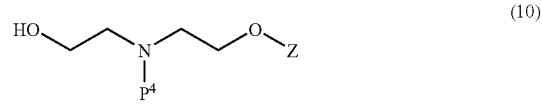

(10)

wherein Z and $P^4$ are the same as defined above, and reacting the compound (10) with halogenophosphite ester to obtain the compound (6).

The present invention also relates to the compound of the following formula:

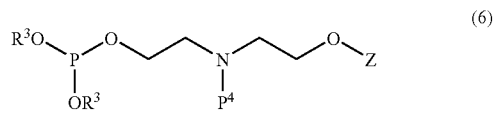

(6)

wherein $R^3$, $P^4$ and Z are the same as defined above.

PREFERABLE MODE FOR CARRYING OUT THE INVENTION

The process for preparing the compound (1) of the present invention is shown in the following reaction scheme.

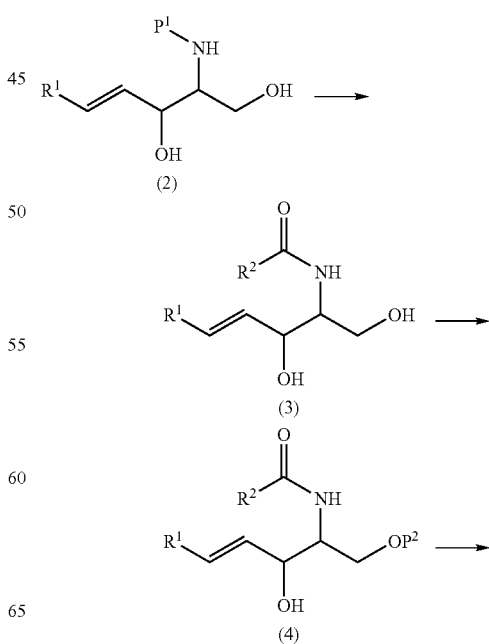

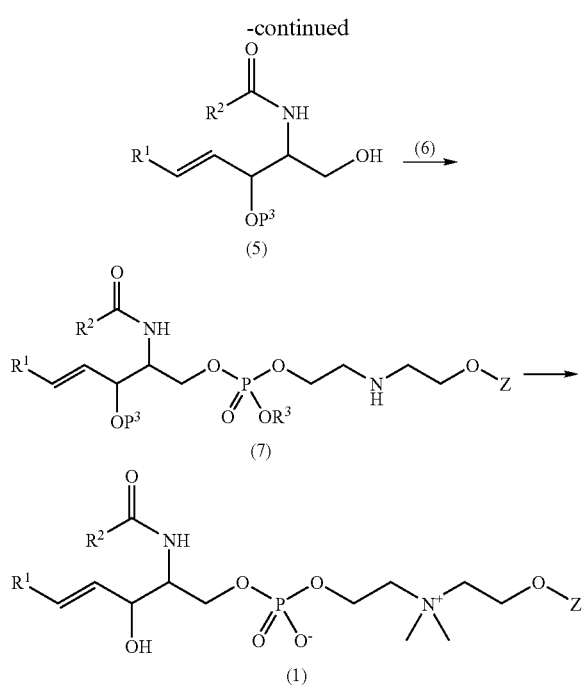

wherein each signal of the formulas is the same as defined above.

(i) The compound (2) is a known compound (See Japanese Patent Publication A 2003-261794). The compound (2) can be unlimitedly prepared by the known method, for example, by reacting benzyl-4-alkoxycarbonyl-2-oxazolidinone with acetylide ion to prepare a ketone, hydrolyzing the carbonyl group to prepare an alcohol, hydrolyzing the triple bond and then hydrolyzing the oxazolidinone ring.

(ii) The compound (3) is prepared by deprotecting the amino protecting group of the compound (2), followed by amidation.

The deprotection of the amino group is conducted by the conventional method for example, when the protecting group is t-butoxycarbonyl group, by using trifluoroacetic acid or diluted hydrochloric acid.

The reagent used for the amidation includes $C_{1-20}$ cyclic or noncyclic acyl chloride such as acetyl chloride, propionyl chloride, butyryl chloride, valeryl chloride, hexanoyl chloride, benzoyl chloride, etc. The amount of the acid chloride is preferably 1 to 3 equivalents to substrate, more preferably 1 to 1.5 equivalents.

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., an ether-solvent such as tetrahydrofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., a nitrile-solvent such as acetonitrile, etc., a halogen-solvent such as dichloromethane, 1,2-dichloroethane, etc., water, and a mixture thereof.

The reaction is from 0° C. to reflux temperature of the solvent, preferably from 0° C. to 25° C.

(iii) The compound (4) is prepared by protecting the primary alcohol of the compound (3).

The preferable reagent for protecting the hydroxy group includes a halogenosilylation agent such as trimethylsilyl chloride, triethylsilyl chloride, t-butyldimethylsilyl chloride, t-butylphenylsilyl chloride, etc. The amount of the reagent is preferably 1 to 5 equivalents to substrate, more preferably 1 to 1.5 equivalents.

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., an ether-solvent such as tetrahydrofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., a nitrile-solvent such as acetonitrile, etc., a halogen-solvent such as dichloromethane, 1,2-dichloroethane, etc., and a mixture thereof.

The reaction temperature is from −78° C. to reflux temperature of the solvent, preferably from −10° C. to 25° C.

(iv) The compound (5) is prepared by protecting the secondary alcohol of the compound (4), followed by deprotecting the protecting group of the primary alcohol.

The reagent for protecting the secondary alcohol includes an organic fatty acid anhydride such as acetic anhydride, propionic anhydride, etc. The amount of the reagent is preferably 1 to 5 equivalents to substrate, more preferably 1 to 3 equivalents.

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., an ether solvent such as tetrahydrofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., a nitrile-solvent such as acetonitrile, etc., a halogen-solvent such as dichloromethane, 1,2-dichloroethane, etc., and a mixture thereof.

The base preferably used in this reaction includes a tertiary amine such as pyridine, pycoline, lutidine, collidine, triethylamine, ethyldiisopropylamine, N,N-dimethylaniline, N,N-diethylaniline, N,N-dimethylaminopyridine, etc. and more preferable one is pyridine, and the base can be served as a solvent.

The reaction temperature is from −78° C. to reflux temperature of the solvent, preferably from 0° C. to reflux temperature of the solvent.

The deprotection of the protecting group of the primary alcohol is conducted by the conventional method for example, when the protecting group is tributyldimethylsilyl group, by using hydrogen fluoride. The amount of the deprotecting reagent is preferably 1 to 10 equivalents to substrate, more preferably 1 to 5 equivalents.

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., an ether-solvent such as tetrahydrofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., a nitrile-solvent such as acetonitrile, etc., a halogen-solvent such as dichloromethane, 1,2-dichloroethaneetc., and a mixture thereof.

(v) The compound (7) is prepared by reacting the compound (5) with a phosphite ester having photoaffinity-labeled group of the following formula:

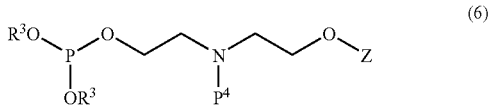

(6)

wherein each signal is the same as defined above, and then, deprotecting the amino protecting group.

The amount of the phosphite ester having photoaffinity-labeled group (6) is preferably 1 to 5 equivalents to substrate, more preferably 1 to 2 equivalents.

The reaction temperature is from −78° C. to reflux temperature of the solvent, preferably from −78° C. to 0° C.

The base used in this reaction includes a tertiary amine such as pyridine, picoline, lutidine, collidine, trimethylamine, triethylamine, ethylisopropylamine, N,N-dimethylaniline, N,N-diethylaniline, N,N-dimethylaminopyridine, etc. and preferable one is pyridine. The amount of the base is preferably 1 to 10 equivalents to substrate, more preferably 1 to 5 equivalents.

The deprotection of the amino group is conducted by the conventional method for example, when the protecting group is t-butoxycarbonyl group, by using an organic acid such as trifluoroacetic acid, etc.

(vi) The photoaffinity-labeled sphingomyelin analog (1) is prepared by hydrolyzing the phosphate of the compound (7), methylating the amino group, and deprotecting the protecting group of the primary alcohol.

The reagent for hydrolyzing the phosphate includes a tertiary amine such as pyridine, picoline, lutidine, collidine, trimethylamine, triethylamine, ethylisopropylamine, N,N-dimethylaniline, N,N-diethylaniline, N,N-dimethylaminopyridine, etc. and preferable one is trimethylamine. The amount of the base is preferably 1 to 10 equivalents to substrate, more preferably 1 to 5 equivalents.

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., an ether-solvent such as tetrahydrofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., an alcohol-solvent such as methanol, ethanol, etc., a nitrile-solvent such as acetonitrile, etc., a halogen-solvent such as dichloromethane, 1,2-dichloroethane, etc., water and a mixture thereof.

The reaction temperature is from 0° C. to reflux temperature of the solvent, preferably from 0° C. to room temperature.

The reagent for methylation includes a methyl halide such as methyl iodide.

The base used includes a tertiary amine such as pyridine, picoline, lutidine, collidine, trimethylamine, triethylamine, ethylisopropylamine, N,N-dimethylaniline, N,N-diethylaniline, N,N-dimethylaminopyridine, etc., a metal carbonate such as potassium carbonate, sodium carbonate, etc., preferably potassium carbonate. The amount of the base is preferably 1 to 20 equivalents to substrate, more preferably 5 to 10 equivalents.

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., an ether-solvent such as tetrahydrofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., an alcohol-solvent such as methanol, ethanol, etc., a nitrile-solvent such as acetonitrile, etc., a halogen-solvent such as dichloromethane, 1,2-dichloroethane, etc., water and a mixture thereof.

The reaction temperature is preferably from 0° C. to reflux temperature of the solvent, more preferably from 0° C. to room temperature.

The reagent preferably used for deprotecting the primary alcohol includes a strong base such as sodium hydroxide, potassium hydroxide, etc.

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., an ether-solvent such as tetrahidorofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., an alcohol-solvent such as methanol, ethanol, etc., a nitrile-solvent such as acetonitrile, etc., a halogen-solvent such as dichloromethane, 1,2-dichloroethane, etc., water and a mixture thereof.

The reaction temperature is from 0° C. to reflux temperature of the solvent, preferably from 0° C. to room temperature.

The process for preparing the compound (6) is explained as follows.

The process for preparing the compound (6) is shown in the following reaction scheme.

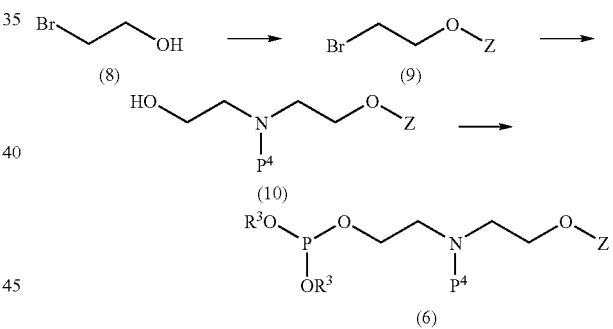

wherein each signal of the formulas is the same as defined above.

(vii) The compound (9) is prepared by reacting the compound (8) and a compound having photoaffinity-labeled group. The compound having photoaffinity-labeled group is not limited as long as it has intramolecular photoaffinity-labeled group, for example, when 4-(3-trifluoromethyl-3H-diaziridin-3-yl)-phenol is used, it can be prepared by the method described in Chem. Pharm. Bull. 826 (1994).

The reagent used in this reaction includes a combination of an azodicarboxylate (e.g., diethyl azodicarboxylate, diisopropyl azodicarboxylate, etc.) and a phosphine compound (e.g., triphenylphosphine, tributylphosphine, etc.).

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., tetrahydrofuran, an ether-solvent such as 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., a nitrile-solvent such as acetonitrile, etc., a halogen-solvent such as dichloromethane, 1,2-dichloroethane, etc. and a mixture thereof.

The reaction temperature is from −78° C. to reflux temperature of the solvent, preferably from 0 to 25° C.

(viii) The compound (10) is prepared by reacting the compound (9) and aminoethanol, followed by protection of the amino group. The amount of the aminoethanol. is preferably 1 to 100 equivalents to substrate, more preferably 10 to 50 equivalents.

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., tetrahydrofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., a nitrile-solvent such as acetonitrile, etc., a halogen-solvent such as dichloromethane, 1,2-dichloroethane, etc. and a mixture thereof.

The reaction temperature is from −78° C. to reflux temperature of the solvent, preferably from 0 to 25° C.

The protection of amino group is conducted by the conventional method for example, when the protecting group is t-butoxycarbonyl group, by using di t-butyl dicarbonate with potassium carbonate.

(ix) The compound (6) is prepared by reacting the compound (10) with a halogenophosphite.

The reagent used in this reaction includes dimethyl chlorophosphite, diethyl chlorophosphite, etc. The amount of the aminoethanol is preferably 1 to 5 equivalents to substrate, more preferably 1 to 2 equivalents.

The solvent preferably used in this reaction includes a hydrocarbon-solvent such as hexane, benzene, toluene, etc., an aprotic polar solvent such as N,N-dimethylformamide, dimethyl sulfoxide, etc., an ester-solvent such as ethyl acetate, butyl acetate, etc., an ether-solvent such as tetrahydrofuran, 1,4-dioxane, 1,2-dimethoxyethane, diglyme, triglyme, diethylene glycol monomethyl ether, etc., a ketone-solvent such as acetone, methyl ethyl ketone, methyl isobutyl ketone, etc., a nitrile-solvent such as acetonitrile, etc., a halogen-solvent such as dichloromethane, 1,2-dichloroethane, etc., water and a mixture thereof.

The reaction temperature is from −78° C. to reflux temperature of the solvent, preferably from −78 to 0° C.

The optically active photoaffinity-labeled sphingomyelin analog (1) with highly optical purity can be prepared by using a starting material, namely the optically active compound (2).

EXAMPLE

The present invention is explained by the following examples, but the present invention should not be limited by the examples.

Synthesis of Ceramide 3a

To N-Boc shingosine (1.28 g, 3.21 mmol) in dichloromethane (16.1 mL) was added at 0° C. trifluoroacetic acid (6.43 mL). The mixture was stirred at the same temperature for 2 hours. After the reaction mixture was neutralized with 1N-aqueous NaOH solution, the mixture was extracted with chloroform. The organic layer was washed with saturated brine, dried over anhydrous magnesium sulfate, and concentrated under reduced pressure. The residue was dissolved in THF-H$_2$O (32.1 mL, 1:1) and thereto added at 0° C. potassium carbonate (2.22 g, 16.1 mmol), and palmitoyl chloride (1.17 mL, 3.85 mmol) successively. The mixture was stirred for 15 minutes. The reaction mixture was neutralized with an aqueous saturated ammonium chloride solution and extracted with chloroform. The organic layer was washed with saturated brine, dried over anhydrous magnesium sulfate and concentrated under reduced pressure. The residue was separated and purified by silica gel chromatography (from 0% to 10% methanol in chloroform) to give ceramide 3a (6.96 g, 99%).

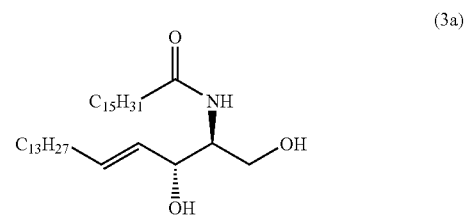

(3a)

[α]$_D^{21.5}$ −3.967 (c=0.963, CHCl$_3$)

IR (KBr disk): 3297, 2915, 1640, 1549, 1468, 1042, 721 cm$^{-1}$ $^1$H NMR (CDCl$_3$, 400 MHz) δ: 6.26 (d, J=7.3 Hz, 1H), 5.77 (dtd, J=1.0, 6.8, 15.4 Hz, 1H), 5.47 (dtd, J=1.2, 6.3, 15.4 Hz, 1H), 4.29 (dd, J=4.6, 4.6 Hz, 1H), 3.90 (m, 2H), 3.69 (dd, J=2.7, 10.7 Hz, 1H), 3.09 (brs, 2H), 2.22 (t, J=7.3 Hz, 2H), 2.05 (td, J=7.1, 7.1 Hz, 2H), 1.63 (m, 2H), 1.37-1.26 (m, 46H), 0.88 (t, J=6.6 Hz, 6H); $^{13}$C NMR (CDCl$_3$, 100 MHz) δ: 174.0, 134.1, 128.9, 74.4, 62.4, 54.8, 36.8, 32.3, 31.9, 29.7, 29.6, 29.5, 29.5, 29.4, 29.3, 29.2, 29.2, 25.8, 22.7, 14.0.

Synthesis of 1-OTBDPS (t-butyldiphenylsililoxy) ceramide 4a

To ceramide 3a (1.19 g, 2.21 mmol) in dichloromethane (44.2 mL) were added at room temperature imidazole (301 mg, 4.42 mmol) and TBDPSCl (t-butyldiphenylsililoxychloride) (0.69 mL, 2.67 mmol) successively. The mixture was stirred at the same temperature for 8 hours. The reaction mixture was poured into ice water and extracted with ethyl acetate. The organic layer was washed with saturated brine, dried over anhydrous magnesium sulfate and concentrated under reduced pressure. The residue was separated and purified by silica gel chromatography (from 17% to 25% ethyl acetate in hexane) to give 1-OTBDPS ceramide 4a (1.41 g, 84%).

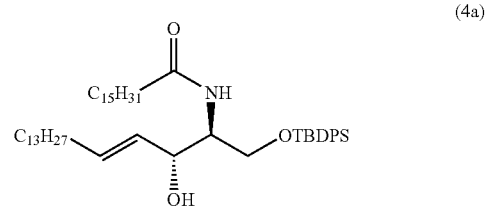

(4a)

[α]$_D^{21.5}$ 6.426 (c=0.985, CHCl$_3$)

IR (Neat): 3316, 2926, 1649, 1466, 1113, 702 cm$^{-1}$ $^1$H NMR (CDCl$_3$, 400 MHz) δ: 7.62 (m, 4H), 7.47-7.36 (m, 6H), 6.09 (d, J=7.8 Hz, 1H), 5.76 (dtd, J=1.2, 6.8, 15.4 Hz, 1H), 5.47 (dd, J=5.9, 15.4 Hz, 1H), 4.19 (m, 1H), 3.97

(m, 1H), 3.95 (dd, J=3.9, 10.5 Hz, 1H), 3.76 (dd, J=3.2, 10.5 Hz, 1H), 3.53 (d, J=8.1 Hz, 1H), 2.15 (t, J=7.3 Hz, 2H), 2.03 (td, J=6.8, 6.8 Hz, 2H), 1.60 (m, 2H), 1.35-1.26 (m, 46H), 1.08 (s, 9H), 0.88 (t, J=6.6 Hz, 3H); $^{13}$C NMR (CDCl$_3$, 100 MHz) δ: 173.3, 135.5, 135.5, 134.8, 133.4, 132.5, 132.4, 130.1, 129.6, 129.0, 127.9, 127.7, 74.2, 64.0, 54.0, 36.8, 32.3, 31.9, 29.7, 29.7, 29.5, 29.5, 29.4, 29.3, 29.3, 29.2, 26.9, 26.6, 25.8, 22.7, 19.2, 14.1.

Synthesis of 3-OAc ceramide 5a

To 1-OTBDPS ceramide 4a (1.41 g, 1.85 mmol) in pyridine (9.23 mL) was added at room temperature acetic anhydride (3.70 mL) and the mixture was stirred for 7 hours. To the reaction solution was added an aqueous saturated copper (II) sulfate solution and the mixture was extracted with ethyl acetate. The organic layer was washed with an aqueous saturated copper (II) sulfate solution and saturated brine and dried over anhydrous magnesium sulfate, followed by concentration under reduced pressure. The residue was dissolved in THF (9.26 mL) and thereto was added Et$_3$N-HF (0.91 mL, 5.56 mmol). The mixture was stirred for a day. The reaction mixture was poured into ice water and extracted with chloroform. The organic layer was washed with an aqueous saturated sodium bicarbonate solution and saturated brine, dried over anhydrous magnesium sulfate and concentrated under reduced pressure. The residue was separated and purified by silica gel chromatography (from 0% to 2% methanol in chloroform) to give 3-OAc ceramide 5a (793 mg, 74%).

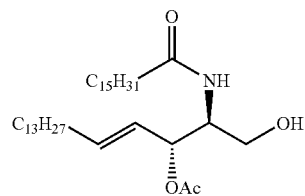

(5a)

[α]$_D^{22.8}$ −20.32 (c=0.775, CHCl$_3$)

IR (KBr disk): 3310, 2919, 2851, 1732, 1638, 1545, 1732, 1638, 1238 cm$^{-1}$ $^1$H NMR (CDCl$_3$, 400 MHz) δ: 6.00 (d, J=8.5 Hz, 1H), 5.77 (td, J=6.8, 15.4 Hz, 1H), 5.46 (dd, J=7.8, 15.4 Hz, 1H), 5.29 (dd, J=7.3, 7.3 Hz, 1H), 4.14 (m, 1H), 3.64 (m, 2H), 2.92 (brs, 1H), 2.17 (dt, J=2.9, 7.3 Hz, 2H), 2.09 (s, 3H), 2.03 (td, J=6.8, 6.8 Hz, 2H), 1.60 (m, 2H), 1.26 (m, 46H), 0.88 (t, J=6.8 Hz, 6H); $^{13}$C NMR (CDCl$_3$, 100 MHz) δ: 173.4,5 171.0, 137.3, 124.7, 74.2, 61.8, 53.2, 36.8, 32.3, 31.9, 29.7, 29.5, 29.5, 29.4, 29.3, 29.3, 29.2, 28.9, 25.7, 22.7, 21.2, 14.1.

ESI HRMS m/z calcd for C$_{36}$H$_{69}$NNaO$_4$ (M$^+$+Na) 602.5124, found 602.5137.

Synthesis of Bromide 9a

To 2-bromoethanol (0.32 mL, 4.45 mmol) in THF (8.9 mL) were added 0° C. triphenylphosphine (1.17 g, 4.45 mmol), DIAD (diisopropyl azodicarboxylate) (0.88 mL, 4.45 mmol) and then phenol P (600 mg, 2.97 mmol) in THF (5.9 mL), and the mixture was stirred at room temperature for 3 hours. The reaction mixture was concentrated under reduced pressure and the residue was separated and purified by silica gel chromatography (1% ethyl acetate in hexane) to give bromide 9a (563 mg, 61%).

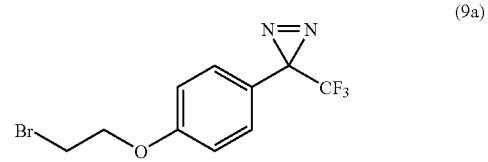

(9a)

IR (Neat): 2934, 1615, 1518, 1184 cm$^{-1}$ $^1$H NMR (CDCl$_3$, 400 MHz) δ: 7.15 (md, J=8.5 Hz, 2H), 6.91 (md, J=9.0 Hz, 2H), 4.28 (t, J=6.1 Hz, 2H), 3.62 (t, J=6.1 Hz, 2H); $^{13}$C NMR (CDCl$_3$, 100 MHz) δ: 159.1, 128.2, 122.2 (q, J$_{C-F}$=275.0 Hz), 121.7, 115.1, 67.9, 28.6.

Synthesis of Alcohol 10a

To bromide 9a (1.47 g, 4.77 mmol) in acetonitrile (14.3 mL) was added at room temperature 2-aminoethanol (8.6 mL, 143 mmol) and the mixture was stirred at the same temperature for 2 days. To the reaction mixture was added water and the mixture was extracted with ethyl acetate. The organic layer was washed with water and concentrated under reduced pressure. The residue was dissolved in THF-H$_2$O (57.6 mL, 1:1) and to the solution were added at 0° C. potassium carbonate (3.29 g, 23.8 mmol) and Boc$_2$O (1.56 g, 7.15 mmol). After stirring for 2.5 hours, the reaction mixture was neutralized with an aqueous saturated ammonium chloride solution, and extracted with ethyl acetate. The organic layer was washed with saturated brine, dried over anhydrous magnesium sulfate and concentrated under reduced pressure. The residue was separated and purified by silica gel chromatography (from 33% to 50% ethyl acetate in hexane) to give alcohol 10a (1.57 g, 85%).

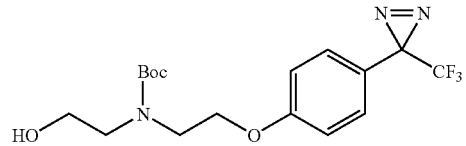

(10a)

IR (Neat): 3437, 2978, 1692, 1520, 1236, 1181, 828 cm$^{-1}$ $^1$H NMR (CDCl$_3$, 400 MHz) δ: 7.15 (md, J=8.5 Hz 2H), 6.90 (md, J=8.8 Hz 2H), 4.16 (brm, 2H), 3.77 (brm, 2H), 3.64 (brm, 2H), 3.51 (brm, 2H), 1.46 (s, 9H); $^{13}$C NMR (CDCl$_3$, 100 MHz) δ: 159.5, 128.2, 123.5 (q, J=274.6 Hz), 120.8, 114.8, 80.6, 66.7, 62.4, 51.7, 48.2, 28.4.

Synthesis of Phosphite Ester 6a

To alcohol 10a (1.40 g, 3.60 mmol) in dichloromethane (18.0 mL) were added at 0° C. pyridine (1.45 mL, 18.0 mmol) and dimethy chlorophosphite (0.924 g, 7.19 mmol) successively, and the mixture was stirred at the same temperature for 10 minutes. The reaction mixture was diluted with diethyl ether, and the precipitate was removed by filtration. The filtrate was washed with water and saturated brine, and concentrated under reduced pressure to give phosphite ester 6a (1.67 g). Without purification the product was served as the next reaction.

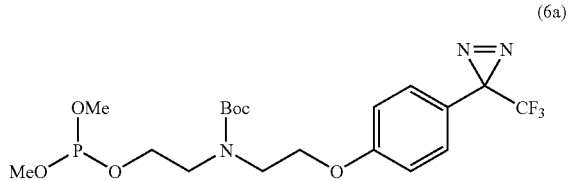

(6a)

Synthesis of Amine 7a

To 3-OAc ceramide 5a (400 mg, 0.690 mmol) and phosphite ester 7a (501 mg, 1.04 mmol) in dichloromethane (13.8 mL) were added at 0° C. pyridine (0.22 mL, 2.76 mmol) and iodine monobromide (285 mg, 1.38 mmol). The mixture was stirred at the same temperature for 4.5 hours. To the reaction mixture was added an aqueous 10% sodium hydrogen sulfite solution, and the mixture was extracted with chloroform. The organic layer was washed with saturated brine, dried over anhydrous magnesium sulfate and concentrated with reduced pressure. The residue was purified by silica gel chromatography (from 0% to 2% methanol in chloroform) to give the crude product. To the crude product was added dichloromethane (6.9 mL) and to the mixture was added at 0° C. trifluoroacetic acid (2.3 mL). The mixture was stirred at the same temperature for 7 hours. The reaction mixture was neutralized with 1N NaOH and extracted with chloroform. The organic layer was washed with saturated brine, dried over anhydrous magnesium sulfate and concentrated under reduced pressure. The residue was separated and purified by silica gel chromatography (from 1% to 20% methanol in chloroform) to give amine 7a (652 mg, 83%).

$J$=6.8, 14.9, 1H), 5.39-5.28 (m, 2H), 4.40 (m, 1H), 4.20-4.07 (m, 6H), 3.79-3.72 (m, 4H), 3.06 (t, $J$=5.1 Hz, 2H), 2.98 (t, $J$=5.1 Hz, 2H), 2.18-2.13 (m, 2H), 2.05 (s, 3H), 2.03-1.97 (m, 2H), 1.58 (m, 2H), 1.32-1.25 (m, 44H), 0.88 (t, $J$=7.1 Hz, 6H); $^{13}$C NMR (CD$_3$OD, 100 MHz) δ: 173.0 (1/2C), 172.9 (1/2C), 169.8 (1/2C), 169.7 (1/2C), 159.7, 137.9 (1/2C), 137.8 (1/2C), 128.1, 124.3, 122.2 (q, $J_{C-F}$=258 Hz), 121.2, 114.9, 73.0, 67.5 (m), 66.4 (m), 64.2, 54.6 (m), 50.9 (m), 49.2 (m), 48.2 (m), 44.4 (m), 36.7, 32.3, 31.9, 29.7, 29.5, 29.5, 29.4, 29.3, 29.3, 29.2, 28.9, 25.6, 22.7, 21.1, 14.1.

ESI HRMS m/z calcd for C$_{49}$H$_{84}$F$_3$N$_4$NaO$_8$P (M$^+$+Na) 967.5887, found 967.5886.

Synthesis of Photoaffinity-labeled Sphingomyelin 1a

To amine 7a (544 mg, 0.576 mmol) in methanol (5.8 mL) was added at room temperature aqueous 30% trimethylamine solution (2.9 mL) and the mixture was stirred for 8 hours. The reaction solution was concentrated under reduced pressure and the residue was dissolved in a mixture solvent of acetonitrile, methanol and water (5.8 mL, 8:1:1). To the solution were added potassium carbonate (796 mg, 5.76 mmol) and methyl iodide (0.58 mL, 9.32 mmol), and the mixture was stirred at room temperature for 1.5 hours. The reaction mixture was diluted with water, and extracted with chloroform and methanol. The organic layer was concentrated under reduced pressure, and the residue was dissolved in methanol (5.8 mL). To the solution was added 2N-aueous potassium hydroxide solution (1.9 mL) and the mixture was stirred for 1 hour. The reaction mixture was diluted with

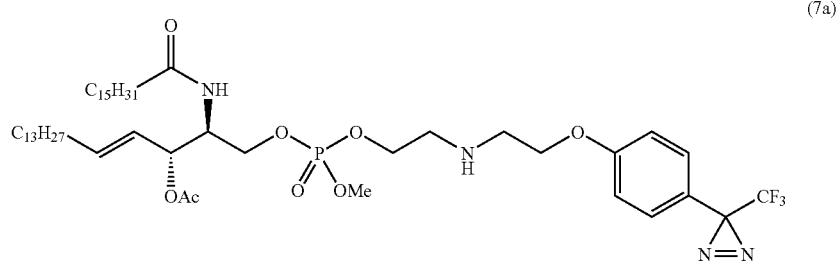

(7a)

[α]$_D^{22.8}$ −12.09 (c=1.050, CHCl$_3$)

IR (KBr disk): 3302, 2919, 1734, 1649, 1520, 1468, 1236, 1182, 1040 cm$^{-1}$ $^1$H NMR (CD$_3$OD, 400 MHz) δ: 7.14 (md, J=8.5 Hz, 2H), 6.91 (md, J=8.8 Hz, 2H), 6.16 (d, J=9.0 Hz, 1H), 5.79 (td, water and extracted with chloroform and methanol. The organic solvent was concentrated under reduced pressure and the residue was separated and purified by silica gel chromatography (from 20% methanol in chloroform to CHCl$_3$:MeOH:H$_2$O=65:25:4) to give photoaffinity-labeled sphingomyelin 1a (329 mg, 62%).

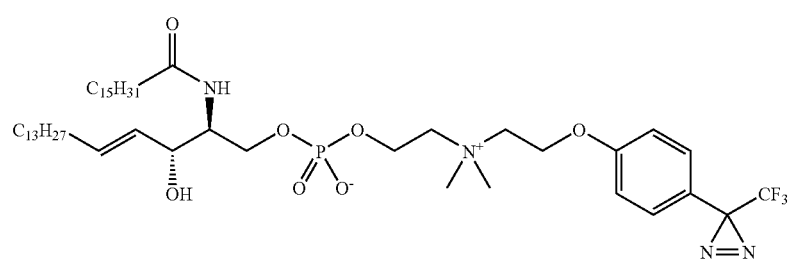

(1a)

[α]$D^{23.0}$ −1.069 (c=0.6550, CH$_3$OH)

IR (KBr disk): 3380, 2920, 1644, 1520, 1468, 1236, 1057 cm$^{-1}$ $^1$H NMR (CD$_3$OD, 400 MHz) δ: 7.90 (d, J=8.8 Hz, 1H), 7.25 (md, J=8.8 Hz, 2H), 7.12 (md. J=9.0 Hz, 2H), 5.69 (td, J=6.8, 14.9 Hz, 1H), 5.44 (dd, J=7.6, 15.4 Hz, 1H), 4.84 (m, 2H), 4.54 (m, 2H), 4.32 (m, 2H), 4.12-3.98 (m, 4H), 3.96 (t, J=4.4 Hz, 2H), 3.77 (t, J=4.4 Hz, 2H), 3.30 (s, 6H), 2.17 (m, 2H), 2.02 (dt, J=6.8, 6.8 Hz, 2H), 1.56 (m, 2H), 1.39-1.29 (m, 46H), 0.90 (t, J=7.1 Hz, 6H); $^{13}$C NMR (CD$_3$OD, 100 MHz) δ: 175.9, 160.2, 135.1, 131.3, 129.5, 123.7 (q, $J_{C-F}$=273.8 Hz), 123.0, 116.5, 72.6, 66.2 (d, $J_{C-P}$=6.6 Hz), 65.9 (d, $J_{C-F}$=5.8 Hz), 65.2, 63.2, 60.3 (d, $J_{C-P}$=5.0 Hz), 55.3 (d, $J_{C-P}$=7.4 Hz), 53.4, 49.0, 37.4, 33.5, 33.1, 30.8, 30.7, 30.6, 30.51, 30.47, 30.4, 27.2, 23.8, 14.5.

ESI HRMS m/z calcd for C$_{48}$H$_{84}$F$_3$N$_4$NaO$_7$P (M$^+$+Na) 939.5927, found 939.5927.

INDUSTRIAL APPLICABILITY

The compounds of the present invention are useful for elucidation of the function and mechanism of sphingomyelinase and are expected as a medicament, especially a diagnosis agent.

What is claimed is:

1. A sphingomyelin analog represented by the following formula:

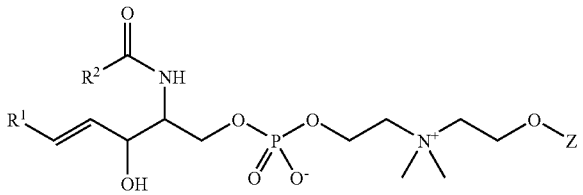

(1)

wherein R$^1$ is C$_{1-20}$ alkyl group, R$^2$ is C$_{1-20}$ alkyl group, aryl group or C$_{1-6}$ alkyl group substituted by aryl group, and Z is photoaffinity-labeled group, or an optically active compound of said analog.

2. The sphingomyelin analog or an optically active compound of said analog according to claim 1 wherein in the formula (1) Z is 4-(3-trifluoromethyl-3H-diaziridin-3-yl)-phenol.

3. A compound represented by the following formula:

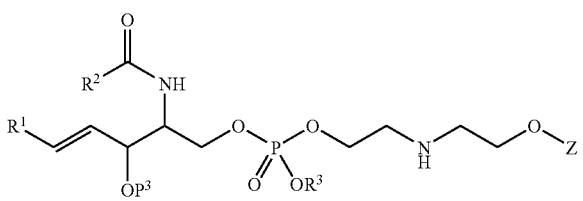

(7)

wherein P$^3$ is hydroxy protecting group, R$^1$ is C$_{1-20}$ alkyl group, R$^2$ is C$_{1-20}$ alkyl group, aryl group or C$_{1-6}$ alkyl group substituted by aryl group, R$^3$ is C$_{1-6}$ alkyl group, and Z is photoaffinity-labeled group.

4. A process for preparing the sphingomyelin analog represented by the following formula:

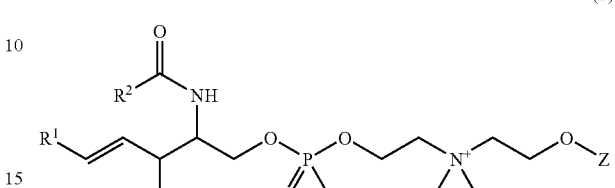

(1)

wherein R$^1$ is C$_{1-20}$ alkyl group, R$^2$ is C$_{1-20}$ alkyl group, aryl group or C$_{1-6}$ alkyl group substituted by aryl group and Z is photoaffinity-labeled group, or an optically active compound of said analog which comprises deprotecting the protected amino group of a compound represented by the following formula:

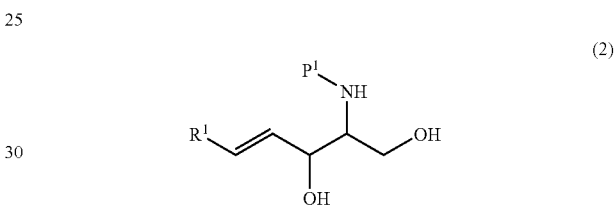

(2)

wherein P$^1$ is amino protecting group, and R$^1$ is the same as defined above, amidating the amino group to obtain a compound of the following formula:

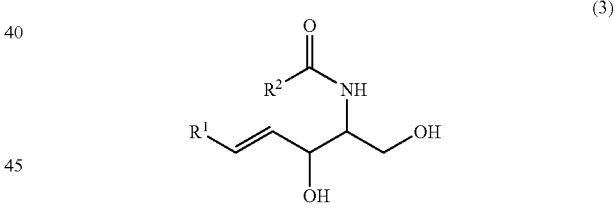

(3)

wherein R$^1$ and R$^2$ are the same as defined above, protecting the primary alcohol to obtain a compound of the following formula:

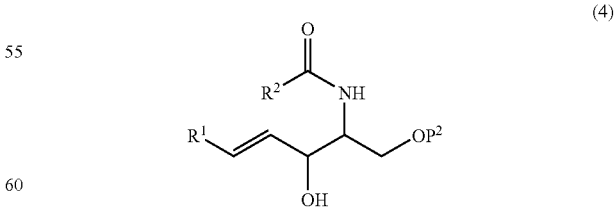

(4)

wherein P$^2$ is hydroxy protecting group, and R$^1$ and R$^2$ are the same as defined above, protecting the secondary alcohol, and deprotecting the protecting group of the primary alcohol to obtain a compound of the following formula:

(5)

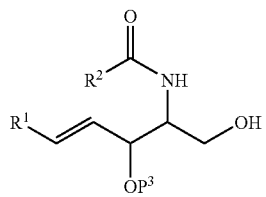

wherein P³ is hydroxy protecting group, R¹ and R² are the same as defined above,
reacting the compound (5) with a compound of the following formula:

(6)

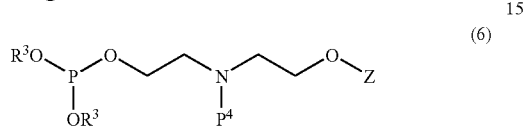

wherein $R^3$ is $C_{1-6}$ alkyl group, $P^4$ is amino protecting group, and Z is the same as defined above,
deprotecting the amino protecting group to obtain a compound of the following formula:

(7)

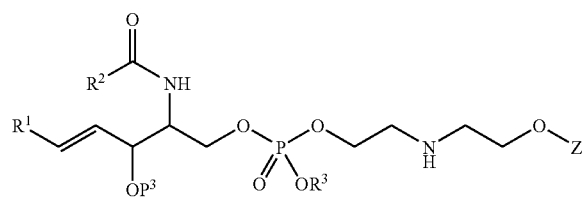

wherein $R^1$, $R^2$, $R^3$, $P^3$ and Z are the same as defined above,
hydrolyzing the phosphate moiety of the compound (7),
methylating the amino group of the compound (7),
and then deprotecting the protecting group of the secondary alcohol of the compound (7) to obtain the compound (1).

5. The process for preparing the compound according to claim 4 wherein Z is 4-(3-trifluoromethyl-3H-diaziridin-3-yl)-phenol.

6. A process for preparing the compound of the following formula:

(6)

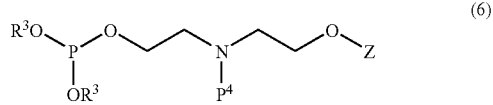

wherein $R^3$ is $C_{1-6}$ alkyl group, $P^4$ is amino protecting group, and Z is photoaffinity-labeled group,
which comprises reacting a compound of the following formula:

(8)

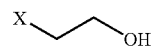

wherein X is halogen atom,
with a compound having photoaffinity-labeled group to obtain a compound of the following formula:

(9)

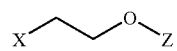

wherein X and Z are the same as defined above,
reacting the compound (9) with 2-aminoethanol,
protecting the amino group to obtain a compound of the following formula:

(10)

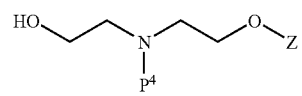

wherein Z and $P^4$ are the same as defined above,
and reacting the compound (10) with halogenophosphite ester to obtain the compound (6).

7. The process for preparing the compound according to claim 6 wherin Z is 4-(3-trifluoromethyl-3H-diaziridin-3-yl)-phenol.

8. A compound of the following formula:

(6)

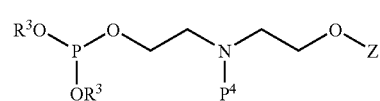

wherein $R^3$ is $C_{1-6}$ alkyl group, $P^4$ is amino protecting group, and Z is photoaffinity-labeled group.

9. The compound according to claim 8 wherein in the formula (6) Z is 4-(3-trifluoromethyl-3H-diaziridin-3-yl)-phenol.

* * * * *